US010687736B2

(12) United States Patent
Yang et al.

(10) Patent No.: US 10,687,736 B2
(45) Date of Patent: Jun. 23, 2020

(54) METHOD OF RECOMMENDING AN ASSISTIVE DEVICE

(71) Applicant: NATIONAL CHIAO TUNG UNIVERSITY, Hsinchu (TW)

(72) Inventors: Bing-Shiang Yang, Hsinchu (TW); Yu-Tang Wen, Toufen (TW); Hsin-Yi Tung, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 201 days.

(21) Appl. No.: 15/446,726

(22) Filed: Mar. 1, 2017

(65) Prior Publication Data
US 2018/0055416 A1 Mar. 1, 2018

(30) Foreign Application Priority Data

Aug. 25, 2016 (TW) .............................. 105127203 A

(51) Int. Cl.
*A61B 5/107* (2006.01)
*A61B 5/00* (2006.01)
*A61B 5/22* (2006.01)

(52) U.S. Cl.
CPC .............. *A61B 5/1071* (2013.01); *A61B 5/22* (2013.01); *A61B 5/4528* (2013.01); *A61B 5/7278* (2013.01)

(58) Field of Classification Search
CPC ... A61B 5/1071; A61B 5/1074; A61B 5/1073; A61B 5/1075; A61B 5/1079;
(Continued)

(56) References Cited

U.S. PATENT DOCUMENTS

2012/0172763 A1* 7/2012 King .................... A61B 5/1071
600/595
2014/0188240 A1* 7/2014 Lang ................... A61F 2/30942
623/22.12
(Continued)

FOREIGN PATENT DOCUMENTS

TW        I223171 B      11/2004
TW        I273449 B       2/2007
(Continued)

OTHER PUBLICATIONS

Johansson, Roland et al., "Predictive Feed-Forward Sensory Control During Grasping and Manipulation in Man", Biomedical Research 14, Supplement 4, 95-106, 1993 (Year: 1993).*
(Continued)

*Primary Examiner* — Matthew Kremer
*Assistant Examiner* — Avery M Foley
(74) *Attorney, Agent, or Firm* — Lewis Roca Rothgerber Christie LLP

(57) ABSTRACT

A method of recommending an assistive device for a user includes: (A) providing a recommendation system that includes a measuring device, an output device and a processing device; (B) the measuring device performing measurement associated with a body part of a user to generate measurement information associated with the body part of the user; (C) the processing device receiving the measurement information from the measuring device, and generating recommendation of an assistive device according to the measurement information; and (D) the output device outputting a message associated with the recommendation.

20 Claims, 5 Drawing Sheets

(58) Field of Classification Search
CPC ... A61B 5/1038; A61B 5/1036; A61B 5/1032; A61B 5/103; A61B 5/1125; A61B 5/1124; A61B 5/1121; A61B 5/1128; A61B 5/22; A61B 5/224; A61B 5/225; A61B 5/4528; A61B 5/4519; A61B 5/4538; A61B 5/4571; A61B 5/7278
See application file for complete search history.

(56) References Cited

U.S. PATENT DOCUMENTS

| | | | | |
|---|---|---|---|---|
| 2015/0374281 | A1* | 12/2015 | Breuille | G06F 19/3475 600/595 |
| 2016/0331308 | A1* | 11/2016 | Zhou | A61B 5/4836 |
| 2017/0027477 | A1* | 2/2017 | Charles | A61B 5/1036 |
| 2017/0231533 | A1* | 8/2017 | Qu | A61B 5/1071 600/409 |
| 2018/0000468 | A1* | 1/2018 | O'Neil | A61B 17/00 |

FOREIGN PATENT DOCUMENTS

| | | |
|---|---|---|
| TW | 200818056 A | 4/2008 |
| TW | 200939143 A | 9/2009 |
| TW | 200948296 A | 12/2009 |
| TW | M408394 U1 | 8/2011 |
| TW | 201436728 A | 10/2014 |

OTHER PUBLICATIONS

A. S. Salles and D. E. Gyi (2013). "An evaluation of personalised insoles developed using additive manufacturing." Journal of Sports Sciences 31(4): 442-450.

C. E. Dombroski, , M. E. Balsdon and A. Froats (2014). "The use of a low cost 3D scanning and printing tool in the manufacture of custom-made foot orthoses: a preliminary study." BMC Research Notes 7(1): 443. (4 pages).

D. Palousek, J. Rosicky, D. Koutny, P. Stoklasek and T. Navrat (2014). "Pilot study of the wrist orthosis design process." Rapid Prototyping Journal 20(1): 27-32.

* cited by examiner

METHOD OF RECOMMENDING AN ASSISTIVE DEVICE

CROSS-REFERENCE TO RELATED APPLICATION

This application claims priority of Taiwanese Patent Application No. 105127203, filed on Aug. 25, 2016.

FIELD

The disclosure relates to a method of recommending an assistive device for a user.

BACKGROUND

Conventionally, when a patient requires an assistive device, a medical professional may determine a suitable one for the patient by evaluating severeness of the patient's symptom(s). However, subjective evaluation, such as feeling the patient's muscle power by hand, may easily result in misjudgment even if the medical professional is highly experienced.

SUMMARY

Therefore, an object of the disclosure is to provide a method of recommending an assistive device for a user based on automatic objective analysis of measurement data.

According to the disclosure, the method includes steps of: (A) providing a recommendation system that includes a measuring device, an output device and a processing device; (B) the measuring device performing measurement associated with a body part of a user to generate measurement information associated with the body part of the user; (C) the processing device receiving the measurement information from the measuring device, and generating recommendation of an assistive device according to the measurement information; and (D) the output device outputting a message associated with the recommendation.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Figure 1:
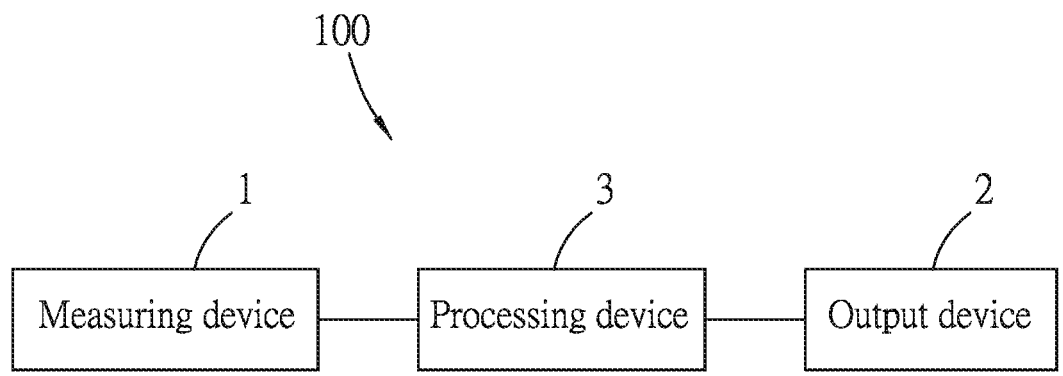
FIG. 1 is a block diagram illustrating a recommendation system for implementing a first embodiment of the method of recommending an assistive device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
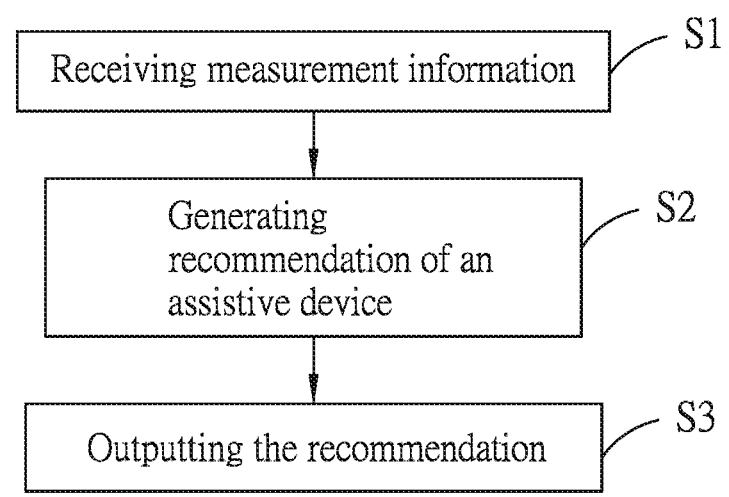
FIG. 2 is a flow chart illustrating steps of the first embodiment.

Referring to FIGS. 1 and 2, the first embodiment of the method for recommending an assistive device for a user includes steps S1-S3, and is implemented using a recommendation system 100 that includes a measuring device 1 for performing measurement associated with a body part of a user to generate measurement information associated with the body part of the user, an output device 2 (e.g., a display device), and a processing device 3 (e.g., a computer) coupled to the measuring device 1 and the output device 2.

In step S1, the processing device 3 receives the measurement information from the measuring device 1. In step S2, the processing device 3 generates recommendation of an assistive device according to the measurement information. In step S3, the processing device 3 controls the output device 2 to output the recommendation.

In a first implementation of the first embodiment, the measuring device 1 includes a three-dimensional (3D) scanner for scanning the user's body, the measurement information includes 3D point cloud information that is generated by the 3D scanner according to a scanning result, and the recommendation includes design information of a customized assistive device that is generated by the processing device 3 according to the 3D point cloud information, that is associated with geometry of the customized assistive device (e.g., a thickness, a margin of each part of the customized assistive device) for the user, and that is provided for assistive device vendors to manufacture the assistive device. In detail, the 3D point cloud information is associated with a plurality of physical states of the body part, and the physical states include different poses the body part is in and/or different external loads (e.g., weights) the body part bears. Accordingly, the geometry of the customized assistive device thus recommended may fit the exterior shape of the user's muscle under different poses or external loads of the body part of the user. For example, the 3D point cloud information may be associated with the exterior shape of the muscles around the thighs, the knees and the shanks when the user is in a standing pose, a seated pose, and intermediate poses between the standing pose and the seated pose, and the geometry of the customized assistive device (e.g., kneecap) thus generated may fit each of the standing pose, the seated pose and the intermediate poses. It is noted that this disclosure is not limited to the abovementioned poses. In practice, poses to be measured during the scanning of the user's body should be determined according to the user's demand (e.g., a pose of the user while at work).

In addition, although the first implementation is exemplified using the 3D scanner, the measuring device 1 may include a magnetic resonance imaging (MRI) device or a computed tomography (CT) scanning device that is used to scan the body part of the user, and the processing device 3 would thus generate the design information according to images generated by the MRI device or the CT scanning device.

Figure 3:
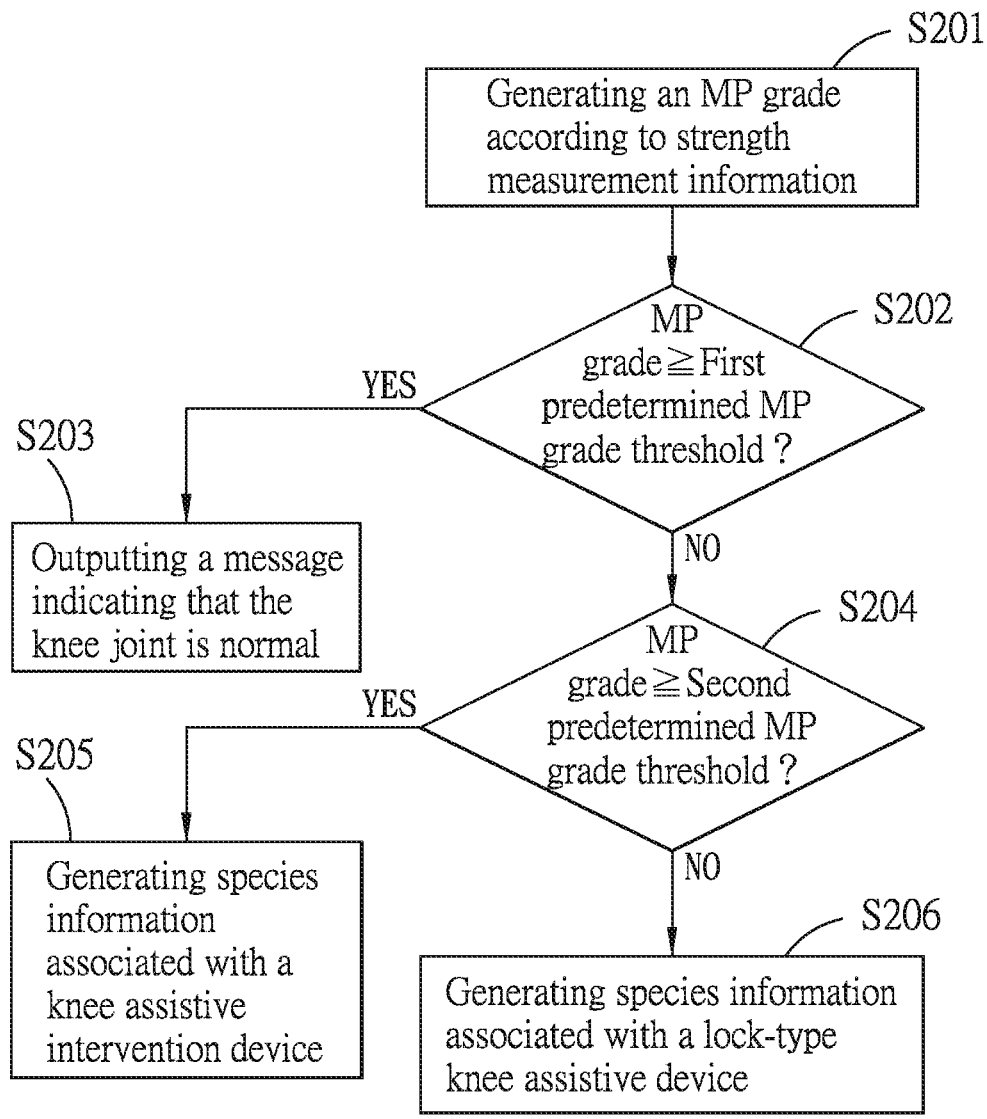
FIG. 3 is a flowchart illustrating one implementation of the first embodiment.

Referring to FIGS. 1-3, a second implementation of the first embodiment according to this disclosure differs from the first implementation in that the measuring device 1 includes a strength measuring device (e.g., a force gauge, a force plate, etc.) which is used to perform measurement associated with a joint of the user to generate strength measurement information associated with the joint of the user, and differs in that the recommendation includes species information which is associated with a modular assistive device and which is generated according to the strength measurement information. The modular assistive device is produced by assistive device vendors according to several predetermined specifications (e.g., sizes).

In the second implementation of the first embodiment, the strength measurement information is associated with a knee joint of the user, and step S2 includes sub-steps S201-S206.

In sub-step S201, the processing device 3 generates a muscle power (MP) grade according to the strength measurement information. Candidate MP grades correspond to a medical research council (MRC) scale as shown in Table 1.

TABLE 1

| MP grade | Description |
| --- | --- |
| 0 | No movement |
| 1 | Only a trace or flicker of movement |
| 2 | Active movement with gravity eliminated |
| 3 | Active movement against gravity without resistance |
| 4 | Active movement against gravity with resistance |
| 5 | Normal power |

In sub-step S202, the processing device 3 determines whether or not the MP grade is higher than or equal to a first predetermined MP grade threshold (e.g., grade 4). The flow goes to sub-step S203 when the determination is affirmative, and goes to sub-step S204 when otherwise.

In sub-step S203, the processing device 3 controls the output device 2 to output a message indicating that the knee joint is normal.

In sub-step S204, the processing device 3 determines whether or not the MP grade is higher than or equal to a second predetermined MP grade threshold (e.g., grade 3) that is lower than the first predetermined MP grade threshold. The flow goes to sub-step S205 when the determination is affirmative, and goes to sub-step S206 when otherwise.

In sub-step S205, the processing device 3 generates the species information associated with a knee assistive intervention device whose joint can rotate freely in the user's saggital plane.

In sub-step S206, the processing device 3 generates the species information associated with a lock-type knee assistive device whose joint is locked at a fixed position (a straight posture of the user).

Figure 4:
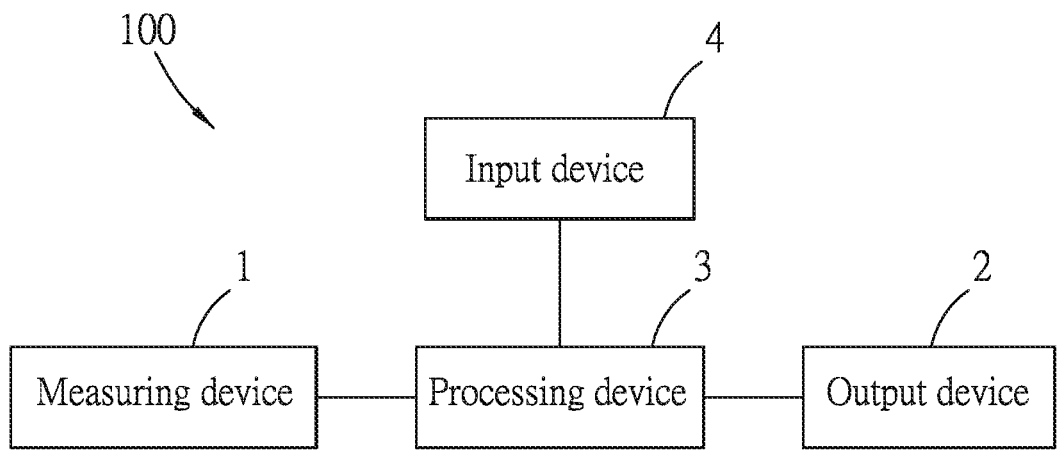
FIG. 4 is a block diagram illustrating a recommendation system for implementing a second embodiment of the method of recommending an assistive device according to the disclosure.
Figure 5:
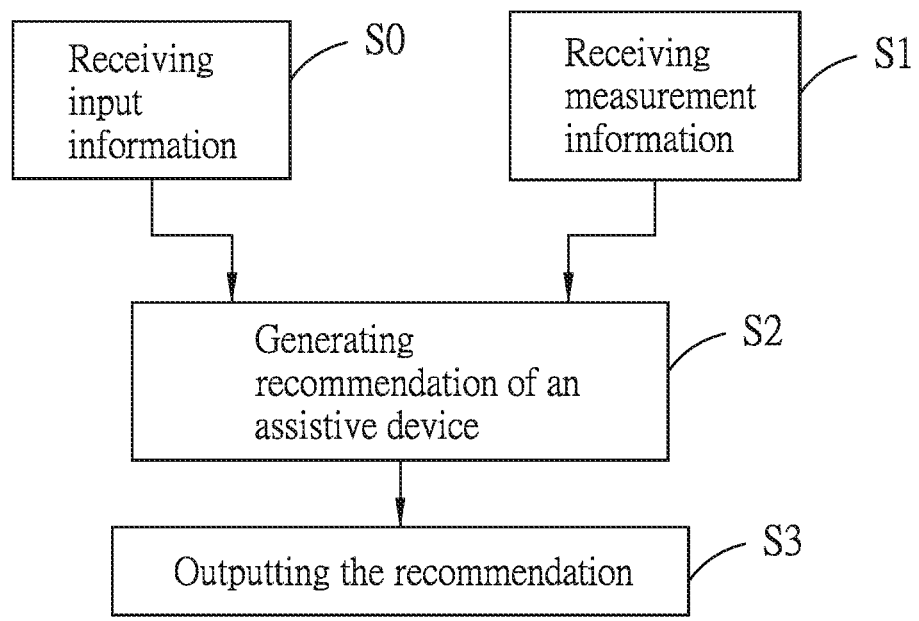
FIG. 5 is a flow chart illustrating steps of the second embodiment.
Figure 6:
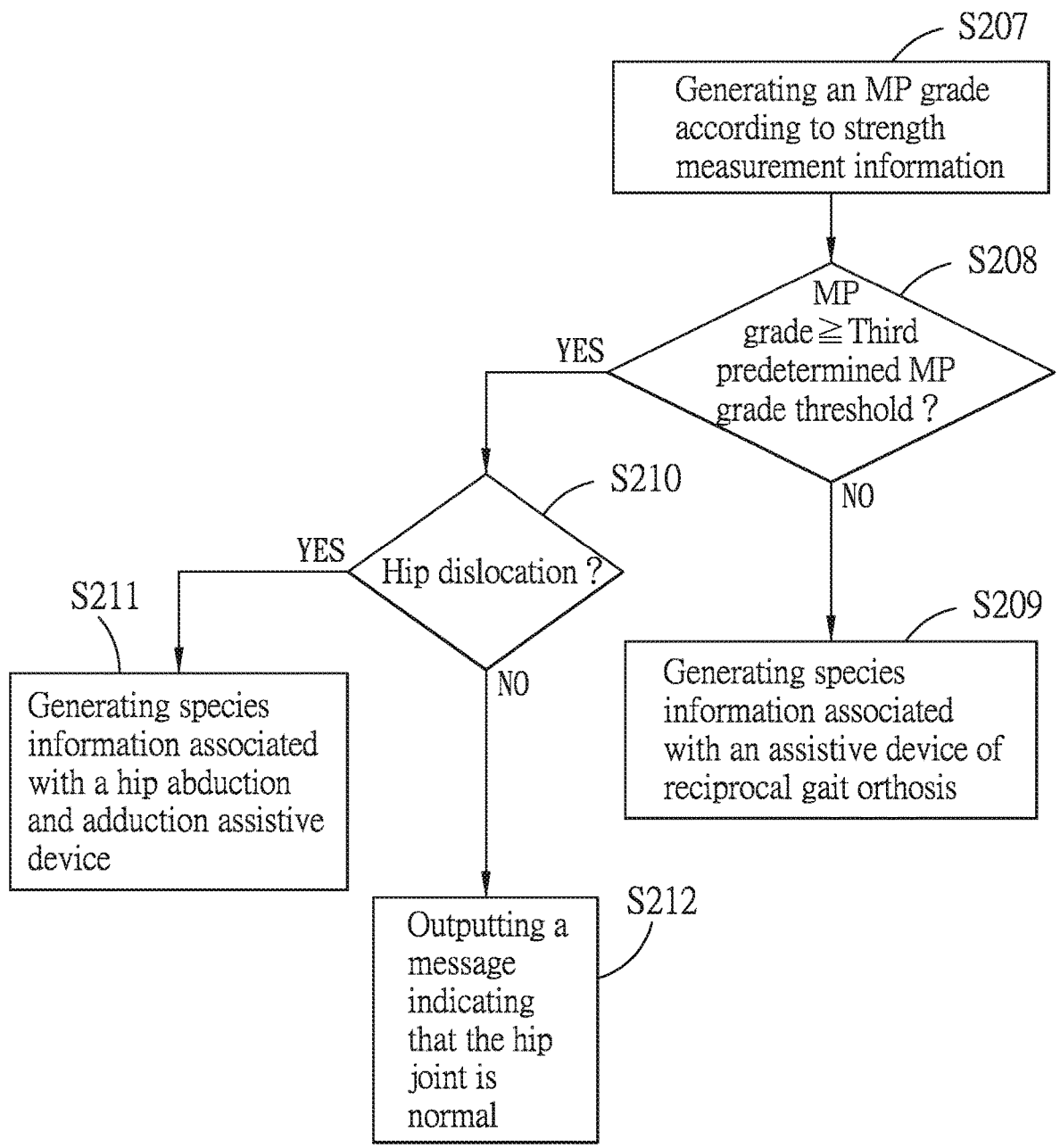
FIG. 6 is a flow chart illustrating a first implementation of the second embodiment.

Referring to FIGS. 4-6, a second embodiment of the method for recommending an assistive device for a user is implemented using a recommendation system 100 that includes, in addition to the abovementioned measuring device 1, the output device 2, and the processing device 3, an input device 4 that is coupled to the processing device 3 and that is for information input by the user. The second embodiment differs from the first embodiment in that the second embodiment further includes step S0 in which the processing device 3 receives, from the input device 4, input information which is inputted through the input device 4 and which is associated with the user, and further differs in that the processing device 3 generates recommendation of an assistive device according to the measurement information and the input information in step S2.

In a first implementation of the second embodiment, the measuring device 1 includes a strength measuring device that is used to perform measurement associated with a joint of the user to generate strength measurement information associated with the joint of the user, and the recommendation includes species information that is associated with a modular assistive device and that is generated according to the strength measurement information and the input information.

In this implementation, the strength measurement information is associated with a hip joint of the user, the input information includes a hip parameter associated with a hip joint condition of the user (e.g., "1" for hip dislocation, and "0" for no hip dislocation), and step S2 includes sub-steps S207-S212.

In sub-step S207, the processing device 3 generates an MP grade according to the strength measurement information.

In sub-step S208, the processing device 3 determines whether or not the MP grade is higher than or equal to a third predetermined MP grade threshold (e.g., grade 3). The flow goes to sub-step S209 when the determination is negative, and goes to sub-step S210 when otherwise.

In sub-step S209, the processing device 3 generates the species information associated with an assistive device of reciprocal gait orthosis.

In sub-step S210, the processing device 3 determines whether or not the hip parameter of the input information indicates hip dislocation. The flow goes to sub-step S211 when the determination is affirmative, and goes to sub-step S212 when otherwise.

In sub-step S211, the processing device 3 generates the species information associated with a hip abduction and adduction assistive device.

In sub-step S212, the processing device 3 controls the output device 2 to output a message indicating that the hip joint is normal.

Figure 7:
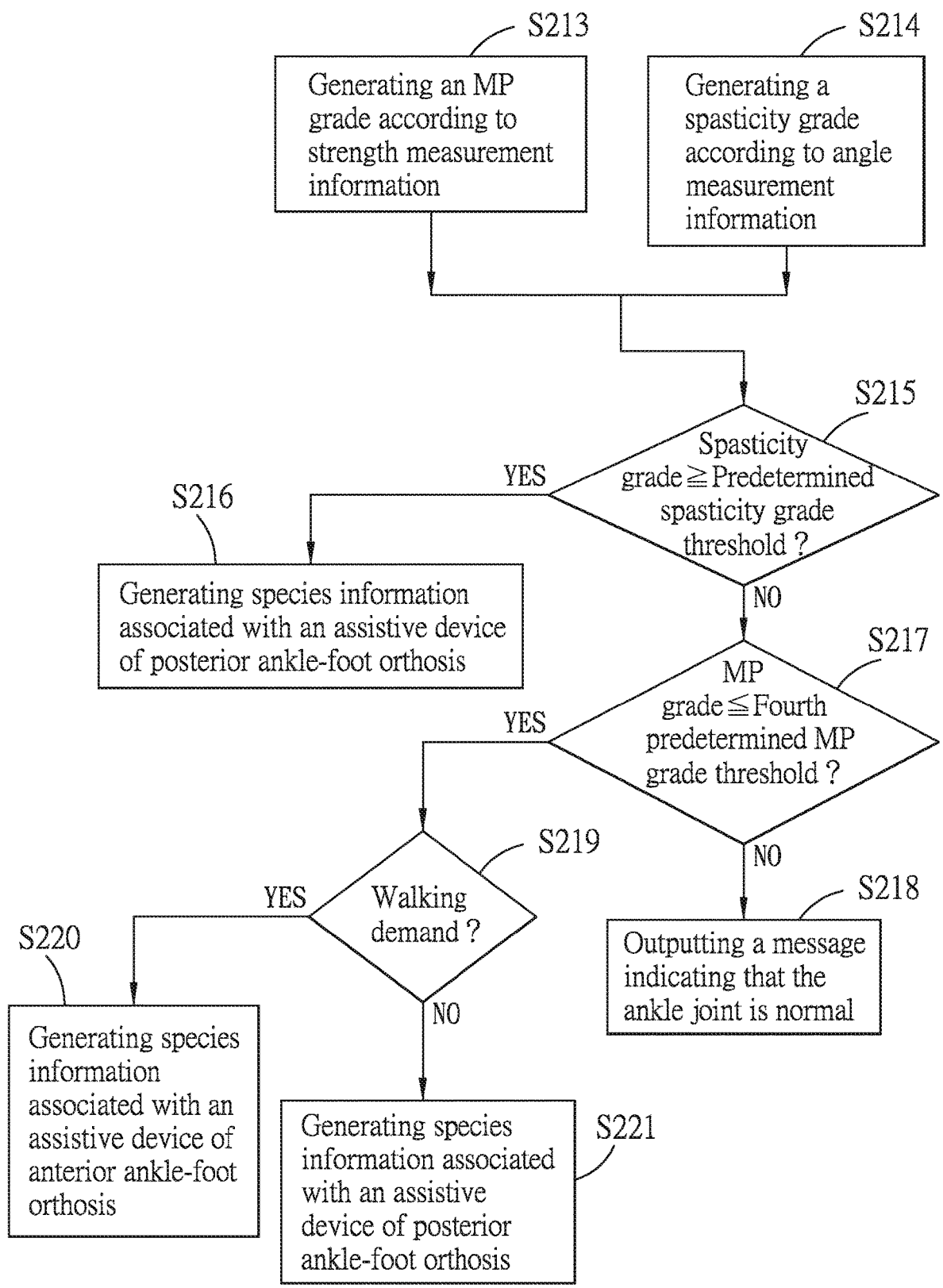
FIG. 7 is a flow chart illustrating a second implementation of the second embodiment.

Referring to FIGS. 4, 5 and 7, a second implementation of the second embodiment differs from the first implementation of the second embodiment in that the measuring device 1 further includes an angle measuring device which is used to perform measurement associated with an angle of the joint of the user to generate angle measurement information, and differs in that the species information is generated according to the strength measurement information, the input information and the angle measurement information.

In this implementation, the strength measuring device and the angle measuring device are used to perform measurements associated with an ankle of the user to generate the strength measurement information and the angle measurement information associated with the ankle of the user; the input information includes a walking parameter associated with a demand to walk of the user (e.g., "0" for no demand to walk and "1" for having demand to walk); and step S2 includes sub-steps S213-S220.

In sub-step S213, the processing device 3 generates an MP grade according to the strength measurement information.

In sub-step S214, the processing device 3 generates a spasticity grade according to the angle measurement information. Candidate spasticity grades correspond to a modified Ashworth scale (MAS) as shown in Table 2.

TABLE 2

| Spasticity grade | Description |
| --- | --- |
| 0 | No increase in muscle tone |
| 1 | Slight increase in muscle tone, manifested by a catch and release, or by minimal resistance at the end of passive range of motion (PROM) |
| 1+ | Slight increase in muscle tone manifested by a catch and release followed by minimal resistance through the |

TABLE 2-continued

| Spasticity grade | Description |
| --- | --- |
| | remainder of the PROM (less than half) |
| 2 | More marked increase in tone throughout most of PROM but parts easily moved |
| 3 | Considerable increase in muscle tone, passive movement difficult |
| 4 | Affected parts rigid in flexion or extension |

In sub-step S215, the processing device 3 determines whether or not the spasticity grade is higher than or equal to a predetermined spasticity grade threshold.

The flow goes to sub-step S216 when the determination is affirmative, and goes to sub-step S217 when otherwise.

In sub-step S216, the processing device 3 generates the species information associated with an assistive device of posterior ankle-foot orthosis.

In sub-step S217, the processing device 3 determines whether or not the MP grade is lower than or equal to a fourth predetermined MP grade threshold (e.g., grade 2). The flow goes to sub-step S218 when the determination is negative, and goes to sub-step S219 when otherwise.

In sub-step S218, the processing device 3 controls the output device 2 to output a message indicating that the ankle joint is normal.

In sub-step S219, the processing device 3 determines whether or not the walking parameter indicates that the user has the demand to walk. The flow goes to sub-step S220 when the determination is affirmative, and goes to sub-step S221 when otherwise.

In sub-step S220, the processing device 3 generates the species information associated with an assistive device of anterior ankle-foot orthosis.

In sub-step S221, the processing device 3 generates the species information associated with an assistive device of posterior ankle-foot orthosis.

In one implementation of the second embodiment, the input information may include a distance parameter associated with a demand in terms of walking distance (e.g., short distance walking, long distance walking) of the user. When the distance parameter indicates the short distance walking, the recommended assistive device may have stronger supporting strength and a heavier weight; and when the distance parameter indicates the long distance walking, the recommended assistive device may have less supporting strength and a lighter weight.

In one implementation of the second embodiment, the input information may include a color parameter associated with a color (e.g., red color, green color, blue color, grey color, brown color, etc.) of the assistive device, and the recommended assistive device corresponds to the color indicated by the color parameter. Accordingly, the user may select a favorite color to increase motivation of using the assistive device.

In one implementation of the second embodiment, the input information may include a position parameter associated with a wearing position of the assistive device (e.g., inside or outside of the trousers), and a wearing position of the recommended assistive device corresponds to that indicated by the position parameter.

In one implementation of the second embodiment, the input information may include a skin parameter associated with a skin condition of the user.

In one implementation of the second embodiment, the input information may include a time parameter associated with a demand regarding a time length of use of the assistive device.

In one embodiment, the measuring device 1 may include a camera device that is used to acquire kinetic image information associated with actions of the user, and the recommendation may include kinetic simulation image information that is associated with the actions of the user when wearing the recommended assistive device and that is generated according to the kinetic image information. This implementation may be realized using techniques relevant to muscle and skeleton simulation. Accordingly, the user may become aware of appearance of wearing the recommended assistive device in advance by watching the kinetic simulation image information outputted by the output device 2.

In one embodiment, the recommendation includes instructions of wearing the recommended assistive device. The instructions may be either still images or kinetic images. Accordingly, the user may clearly understand how to wear the recommended assistive device.

In one embodiment, the measuring device 1 may include a pressure measuring device that is used to perform measurement associated with a plantar pressure of the user to generate pressure measurement information, and the recommended assistive device would thus be capable of sustaining the plantar pressure of the user.

In one embodiment, the measuring device 1 may include a motion capture system, an inertial measurement device, a force plate and an electromyography (EMG) device.

To sum up, the embodiments according to this disclosure use the processing device 3 to provide, based on the measurement information (e.g., 3D point cloud information, strength measurement information, angle measurement information, kinetic image information, pressure measurement information, etc.) and/or the input information (e.g., hip parameter, walking parameter, distance parameter, color parameter, position parameter, skin parameter, time parameter, etc.), the recommendation associated with an assistive device for the user (e.g., design information of a customized assistive device, species information of a modular assistive device, kinetic simulation image information, instructions of wearing the recommended assistive device, etc.), so the assistive device thus recommended may fit the requirement of the user.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method of recommending an assistive device for a user, comprising steps of:
   (A) providing a recommendation system that includes a measuring device, an output device and a processing device;
   (B) the measuring device performing measurement associated with a body part of the user to generate measurement information;
   (C) the processing device receiving the measurement information from the measuring device, and generating recommendation of the assistive device according to the measurement information;
   (D) the output device outputting a message associated with the recommendation; and
   (E) providing the assistive device for the user based on the message outputted by the output device;
   wherein the measurement information includes three-dimensional information associated with geometry of the body part in a plurality of physical states, and each of the physical states is an individual load amount born by the user;
   wherein the recommendation includes design information of a customized assistive device that is associated with geometry of the customized assistive device for the user;
   wherein the measuring device includes a strength measuring device, step (B) includes the strength measuring device performing measurement associated with a joint of the user to generate strength measurement information associated with the joint of the user, and the recommendation includes species information that is associated with a modular assistive device and that is generated according to the strength measurement information;
   wherein the strength measurement information is associated with a knee joint of the user, and step (C) includes sub-steps of:
   (C01) the processing device generating a muscle power grade according to the strength measurement information;
   (C02) the processing device generating the species information for a knee assistive intervention device when the processing device determines that the muscle power grade is lower than a first predetermined muscle power grade threshold and is higher than or equal to a second predetermined muscle power grade threshold that is lower than the first predetermined muscle power grade threshold; and
   (C03) the processing device generating the species information for a lock-type knee assistive device when the processing device determines that the muscle power grade is lower than the second predetermined muscle power grade threshold.

2. The method of claim 1, wherein the measuring device includes a three-dimensional (3D) scanner, the three-dimensional information of the measurement information is 3D point cloud information, and step (C) includes the processing device generating the design information according to the 3D point cloud information.

3. The method of claim 1, wherein the measuring device includes a camera device, step (B) includes the camera device acquiring kinetic image information associated with actions of the user, and the recommendation includes kinetic simulation image information that is associated with the actions of the user when wearing the assistive device and that is generated according to the kinetic image information.

4. The method of claim 1, wherein the measuring device includes a pressure measuring device, and step (B) includes the pressure measuring device performing measurement associated with a plantar pressure of the user to generate pressure measurement information.

5. A method of recommending an assistive device for a user, comprising steps of:
   (A) providing a recommendation system that includes a measuring device, an output device and a processing device;
   (B) the measuring device performing measurement associated with a body part of the user to generate measurement information;
   (C) the processing device receiving the measurement information from the measuring device, and generating recommendation of the assistive device according to the measurement information;
   (D) the output device outputting a message associated with the recommendation; and
   (E) providing the assistive device for the user based on the message outputted by the output device;
   wherein the measurement information includes three-dimensional information associated with geometry of the body part in a plurality of physical states, and each of the physical states is an individual load amount born by the user;
   wherein the recommendation includes design information of a customized assistive device that is associated with geometry of the customized assistive device for the user;
   wherein the recommendation system further includes an input device;
   wherein step (C) further includes the processing device receiving, from the input device, input information that is inputted through the input device and that is associated with the user, and generating recommendation of the assistive device according to the measurement information and the input information;
   wherein the measuring device includes a strength measuring device, step (B) includes the strength measuring device performing measurement associated with a joint of the user to generate strength measurement information associated with the joint of the user, and the recommendation includes species information that is associated with a modular assistive device and that is generated according to the input information and the strength measurement information; and
   wherein the strength measurement information is associated with a hip joint of the user, the input information includes a hip parameter associated with a hip joint condition of the user, and step (C) includes sub-steps of:
   (C01) the processing device generating a muscle power grade according to the strength measurement information;
   (C02) the processing device generating the species information for a hip abduction and adduction assistive device when the processing device determines that the muscle power grade is higher than or equal to a predetermined muscle power grade threshold and that the hip parameter indicates hip dislocation; and
   (C03) the processing device generating the species information for an assistive device of reciprocal gait orthosis when the processing device determines that the muscle power grade is lower than the predetermined muscle power grade threshold.

6. The method of claim 5, wherein the input information includes a distance parameter associated with a demand in terms of walking distance of the user.

7. The method of claim 5, wherein the input information includes a color parameter associated with a color of the assistive device.

8. The method of claim 5, wherein the input information includes a skin parameter associated with a skin condition of the user.

9. The method of claim 5, wherein the input information includes a time parameter associated with a demand regarding time length of use of the assistive device.

10. The method of claim 5, wherein the measuring device includes a three-dimensional (3D) scanner, the three-dimensional information of the measurement information is 3D point cloud information, and step (C) includes the processing device generating the design information according to the 3D point cloud information.

11. The method of claim 5, wherein the measuring device includes a camera device, step (B) includes the camera device acquiring kinetic image information associated with actions of the user, and the recommendation includes kinetic simulation image information that is associated with the actions of the user when wearing the assistive device and that is generated according to the kinetic image information.

12. The method of claim 5, wherein the measuring device includes a pressure measuring device, and step (B) includes the pressure measuring device performing measurement associated with a plantar pressure of the user to generate pressure measurement information.

13. A method of recommending an assistive device for a user, comprising steps of:
(A) providing a recommendation system that includes a measuring device, an output device and a processing device;
(B) the measuring device performing measurement associated with a body part of the user to generate measurement information;
(C) the processing device receiving the measurement information from the measuring device, and generating recommendation of the assistive device according to the measurement information;
(D) the output device outputting a message associated with the recommendation; and
(E) providing the assistive device for the user based on the message outputted by the output device;
wherein the measurement information includes three-dimensional information associated with geometry of the body part in a plurality of physical states, and each of the physical states is an individual load amount born by the user;
wherein the recommendation includes design information of a customized assistive device that is associated with geometry of the customized assistive device for the user;
wherein the recommendation system further includes an input device;
wherein step (C) further includes the processing device receiving, from the input device, input information that is inputted through the input device and that is associated with the user, and generating recommendation of the assistive device according to the measurement information and the input information;
wherein the measuring device includes a strength measuring device, step (B) includes the strength measuring device performing measurement associated with a joint of the user to generate strength measurement information associated with the joint of the user, and the recommendation includes species information that is associated with a modular assistive device and that is generated according to the input information and the strength measurement information;
wherein the measuring device further includes an angle measuring device, step (B) further includes the angle measuring device performing measurement associated with an angle of the joint of the user to generate angle measurement information, and the species information is generated according to the input information, the strength measurement information and the angle measurement information; and
wherein step (B) includes the strength measuring device and the angle measuring device performing measurement associated with an ankle of the user to generate the strength measurement information and the angle measurement information associated with the ankle of the user, the input information includes a walking parameter associated with a demand to walk of the user, and step (C) includes sub-steps of:
(C01) the processing device generating a muscle power grade according to the strength measurement information;
(C02) the processing device generating a spasticity grade according to the angle measurement information;
(C03) the processing device generating the species information for an assistive device of posterior ankle-foot orthosis when the processing device determines that the spasticity grade is higher than or equal to a predetermined spasticity grade threshold;
(C04) the processing device generating the species information for an assistive device of anterior ankle-foot orthosis when the processing device determines that the spasticity grade is lower than the predetermined spasticity grade threshold, that the muscle power grade is lower than or equal to a predetermined muscle power grade threshold, and that the walking parameter indicates that the user has the demand to walk; and (C05) the processing device generating the species information for the assistive device of posterior ankle-foot orthosis when the processing device determines that the spasticity grade is lower than the predetermined spasticity grade threshold, that the muscle power grade is lower than or equal to the predetermined muscle power grade threshold, and that the walking parameter indicates that the user has no demand to walk.

14. The method of claim 13, wherein the input information includes a distance parameter associated with a demand in terms of walking distance of the user.

15. The method of claim 13, wherein the input information includes a color parameter associated with a color of the assistive device.

16. The method of claim 13, wherein the input information includes a skin parameter associated with a skin condition of the user.

17. The method of claim 13, wherein the input information includes a time parameter associated with a demand regarding time length of use of the assistive device.

18. The method of claim 13, wherein the measuring device includes a three-dimensional (3D) scanner, the three-dimensional information of the measurement information is 3D point cloud information, and step (C) includes the processing device generating the design information according to the 3D point cloud information.

19. The method of claim 13, wherein the measuring device includes a camera device, step (B) includes the camera device acquiring kinetic image information associated with actions of the user, and the recommendation includes kinetic simulation image information that is associated with the actions of the user when wearing the assistive device and that is generated according to the kinetic image information.

20. The method of claim 13, wherein the measuring device includes a pressure measuring device, and step (B) includes the pressure measuring device performing measurement associated with a plantar pressure of the user to generate pressure measurement information.

* * * * *